US00PP15255P2

(12) United States Plant Patent
Salter

(10) Patent No.: US PP15,255 P2
(45) Date of Patent: Oct. 19, 2004

(54) ***MUSA* PLANT NAMED 'LITTLE PRINCE'**

(50) Latin Name: *Musa acuminata*
Varietal Denomination: Little Prince

(76) Inventor: Randolph Salter, 8309 Pinecrest Rd., Raleigh, NC (US) 27613-4532

( * ) Notice: Subject to any disclaimer, the term of this patent is extended or adjusted under 35 U.S.C. 154(b) by 0 days.

(21) Appl. No.: 10/668,016

(22) Filed: Sep. 23, 2003

(51) Int. Cl.[7] ..... A01H 5/00
(52) U.S. Cl. ..... Plt./160
(58) Field of Search ..... Plt./160

*Primary Examiner*—Anne Marie Grunberg
*Assistant Examiner*—June Hwu

(57) ABSTRACT

A new cultivar of *Musa* named 'Little Prince' that is characterized by a very dwarf, compact habit, thick trunk, low light level tolerance and thicker, darker green leaves. In combination these traits set 'Little Prince' apart from all other existing varieties of *Musa* known to the inventor.

1 Drawing Sheet

Genus: *Musa.*
Species: *acuminata.*
Denomination: Little Prince.

BACKGROUND OF THE INVENTION

The present invention relates to a new and distinct cultivar of *Musa acuminata,* hereinafter referred to by the cultivar name, 'Little Prince'.

The inventor owns a nursery in Raleigh, N.C., and has a special interest in sub-tropical plants that can been grown as landscape plants in the south-east region of the United States, including the genera *Musa* and *Canna.* The inventor is a commercial grower of *Musa* including the dwarf cultivars of *Musa acuminata* known as *Musa acuminata* 'Novak' (unpatented), *Musa acuminata* 'Dwarf Cavendish' (unpatented) and *Musa acuminata* 'Super Dwarf Cavendish' (unpatented).

'Little Prince' was discovered in the inventor's nursery in Raleigh, N.C. as one plant in one cell within a cell tray of tissue culture stage III (rooted in growing medium) plants of *Musa acuminata* 'Dwarf Cavendish' (unpatented). The inventor observed that the plant in this particular cell had four pseudostems (tightly wrapped leaf sheaves giving the appearance of a single stem or trunk) arising from a common piece of callous tissue. The inventor observed the entire set of plants from the cell tray including the plant with four pseudostems. After 3 months of further growth, the plant with four pseudostems failed to obtain the height common to the rest of the crop. The inventor transplanted into separate 1-gallon pots the entire set of plants in the cell tray. At six months after transplanting, the one plant with the four pseudostems was approximately 10 inches tall, whereas the rest of the plants, being grown under identical conditions, had achieved a height of approximately 5 feet. The inventor concluded that the said one plant, now named 'Little Prince', with its four pseudostems was a naturally occurring genetically mutated dwarf sport of the presumed parent *Musa acuminata* 'Dwarf Cavendish'. When compared with 'Dwarf Cavendish', 'Little Prince' remains short in successive seasons of growth whereas 'Dwarf Cavendish' continues to grow at a faster rate until reaching a mature height of approximately 8–10 feet, that is approximately six times the height of a mature, same age, plant of 'Little Prince'.

In April 1996, the inventor first asexually propagated 'Little Prince' by division and separation of the pseudostems at the rhizomatous base. Upon establishment of each division, the inventor determined that 'Little Prince' had been reproduced true to type. The inventor commissioned a tissue culture laboratory in Rancho Santa Fe, Calif., to commence multiplication in vitro of 'Little Prince' which has continued, both in vitro and in its subsequent growth, to remain stable and true to type in successive generations.

The inventor has observed that 'Little Prince' begins to exhibit unique characteristics of thicker and darker green leaves at approximately 4–5 months from deflasking. After a further period of approximately six months in growing medium (that is, 10–12 months after deflasking) the foliage of 'Little Prince' appears as a flattened rosette of leaves, at which stage the variety is approximately 10"–12" tall, measured from the top of the growing medium. The comparison variety known as 'Novak' at this same stage exhibits leaves which are still unfurling, and are longer and without any crown formation. In second and subsequent growing years, the differences between 'Little Prince' and 'Novak' become yet more apparent as follows:

The leaves of 'Little Prince' will grow to no more than 14"–18" in blade length; Novak grows to 24"–30". The "trunk" of 'Little Prince' slows its extension and will grow typically to a height of 18 inches, and to no more than 24 inches; Novak will extend to a height typically of 40 inches to 48 inches, and sometimes taller. All parts of 'Little Prince' appear dwarfed in scale compared with other dwarf varieties of *Musa acuminata* known to the inventor.

The leaves of 'Little Prince' have been observed to be thicker making Little Prince a better houseplant. This same thickness renders the foliage of 'Little Prince' to be much more resistant to the wind shredding that is common to all bananas including Novak when used in the landscape.

'Little Prince' has never been observed to flower.

Indicative comparisons of final plant height of 'Little Prince' and of other dwarf varieties of *Musa acuminata* known to the inventor are as follows:

| | |
|---|---|
| Cavendish | 12–15 feet |
| Dwarf Cavendish | 8–10 feet |
| Super Dwarf Cavendish | 4–6 feet |
| Novak | 3½–5 feet |
| Little Prince | 1½–2½ feet |

SUMMARY OF THE INVENTION

The following traits have been repeatedly observed and represent the distinguishing characteristics of the new *Musa* variety known as 'Little Prince'. These traits in combination distinguish 'Little Prince' from all other existing varieties of *Musa* known to the inventor. 'Little Prince' has not been tested under all possible conditions and phenotypic differences may be observed with variations in environmental, climatic, and cultural conditions, however, without any variance in genotype.

1. *Musa* 'Little Prince' is short in height, with a mature height of 24 to 30 inches.
2. *Musa* 'Little Price' has not been observed to flower.
3. *Musa* 'Little Prince' exhibits thicker leaves than other dwarf *Musa*.
4. *Musa* 'Little Prince' exhibits darker green leaves than the species.
5. *Musa* 'Little Prince' exhibits low light tolerance.
6. *Musa* 'Little Prince' forms a crown rosette of leaves at a young age as opposed to extending the length of the two pseudostems as is typical of *Musa acuminata*.
7. *Musa* 'Little Prince' is approximately $1/16^{th}$ the mature size of the parent plant.
8. *Musa* 'Little Prince' exhibits a thicker trunk for its height, than other dwarf *Musa,* especially at its base.
9. *Musa* 'Little Prince' exhibits a plant structure with leaves that appear to layer in a clockwise fashion, almost on top of each other.
10. *Musa* 'Little Prince' is suitable as a container or landscape plant and as a decorative indoor plant.

BRIEF DESCRIPTION OF THE DRAWING

The accompanying color drawing illustrates the overall appearance of an approximately 30 months old plant (from a tissue culture plantlet) of the new *Musa* variety 'Little Prince', showing the color as true as it is reasonably possible to obtain in colored reproductions of this type. The drawing on sheet 1 illustrates the thick trunk and extremely short internodes that is typical of this plant. Colors in the drawing may differ from the color values cited in the detailed botanical description, which accurately describe the actual colors of the new variety 'Little Prince'. The drawing was made using conventional photographic techniques and although foliage colors may appear different from actual colors due to light reflectance, they are as accurate as is possible by conventional photography.

BOTANICAL DESCRIPTION OF THE PLANT

The following is a detailed description of the new *Musa* cultivar named 'Little Prince'. Observations, measurements, color determinations, and comparisons were made at Oasis Plant Farms, LLC in Raleigh, N.C. from three to six year old plants growing in 2 gallon containers. Color determinations are in accordance with The 2001 Royal Horticultural Society Colour Chart from London, England, except where general color terms of ordinary dictionary significance are used. The growing requirements are similar to the species.

Botanical classification: *Musa acuminata* 'Little Prince'.
Commercial classification: Ornamental.
Species: *acuminata.*
Common name: Banana.
Use: Ornamental plant suitable as an indoor potted plant, landscape planting, and outdoor container plant.
Type: Tender perennial.
Parentage: 'Little Prince' found in tray of tissue culture stage III plants of *Musa acuminata* 'Dwarf Cavendish'.
Growth rate: Slow growing.
Growth habit: Upright, compact habit.
Plant height (at maturity): 70 cm. in height.
Plant width (at maturity): 60–70 cm. in width.
Hardiness: USDA Zone 7b to 11.
Propagation: Asexual propagation is accomplished using rhizome division and tissue culture.
Root system: Fleshy.
Pollination requirements: Not applicable.
Sexuality: Sterile.
Cultural requirements: Plant in rich humus at a pH between 5.7 and 6.5. The light requirements extend over a wide range 1000–5,000 foot candles. Grow in partial shade.
Crop time: 2–3 weeks to develop roots on an initial cutting at a recommended air temperature of 23–30 Centigrade, and approximately 5 months to reach commercial size.
Seasonal interest: Spring, summer outdoors and year round for indoor.
Diseases and pests: Some susceptibility to spider mites. No serious problems known to the inventor.
Stem or trunk: Pseudostem comprised of unfurled leaf petioles.
*Shape.*—Round, swollen at base.
*Size.*—Length at maturity: 45–60 cm. Diameter at maturity: upper four-fifths of length: 5–8 cm. Basal portion: swelling to 8–10 cm.
*Surface.*—Smooth, glossy, waxy.
*Color.*—Upper four-fifths of length: ranges from 137C to 139A. Basal portion: ranges from 139A to 187A.
Foliage:
*Type.*—Evergreen.
*Leaf shape.*—Wide lanceolate.
*Leaf length.*—50 cm.
*Leaf width.*—15–23 cm.
*Leaf arrangement.*—Whorled.
*Leaf apex.*—Lanceolate with a drip tip.
*Leaf base.*—Rounded, asymmetric.
*Leaf division.*—Simple.
*Leaf attachment.*—Petiolate sheath forming pseudostem.
*Petiole.*—Petiole margin winged; margin erect or open; not clasping pseudostem. Petiole margin wings narrow, smooth, waxy, pale green close to 144A. Edge of petiole margin: translucent, colorless (no color line present). Petiole length (when detached from pseudostem): 20–45 cm. Petiole diameter: 2–4 cm. Petiole color: Newest growth closest to 144A. Older foliage 137C. Some rust-colored speckling has been observed: closest to 173A. Petiole surface: Smooth, a little waxy.
*Leaf margins.*—Entire.
*Leaf color* (*adaxial surface*).—Closest to 139A. At higher light intensity, reddish blotches, color 187A, may cover up to one fifth of surface area of uppermost leaves; lower leaves unblotched.
*Leaf color* (*abaxial surface*).—Closest to 137C.
*Leaf surface* (*adaxial surface*).—Glabrous.
*Leaf surface* (*abaxial surface*).—Glabrous waxy.
*Venation pattern.*—Pinnately parallel.
*Color of veins.*—144A.
*Leaf fragrance.*—None observed.
*Stipules.*—None observed.
Flower: No flower has been observed.

I claim:

1. A new and distinct variety of *Musa* plant named 'Little Prince' as described and illustrated.

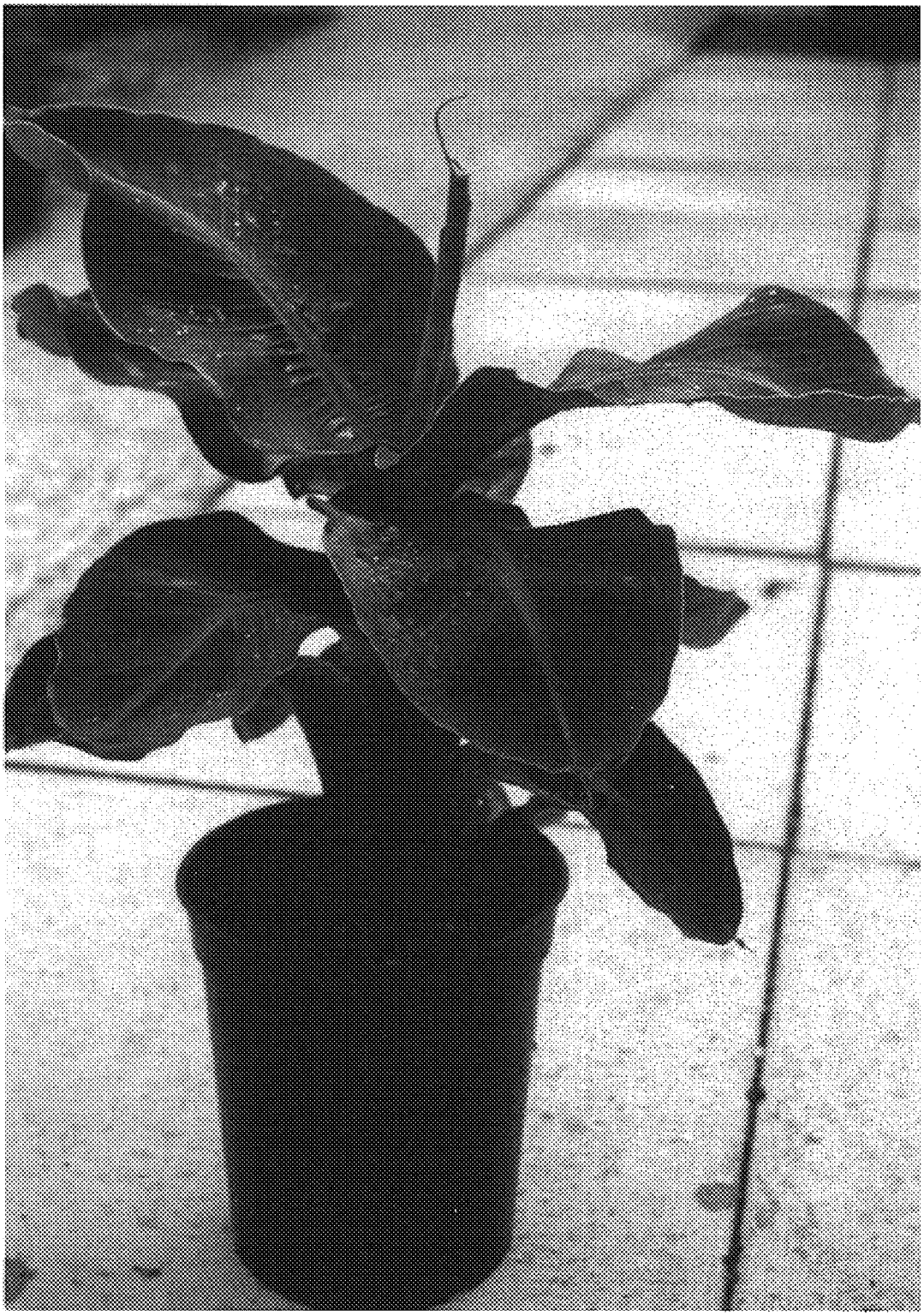

* * * * *